(12) United States Patent
Cho et al.

(10) Patent No.: US 11,041,190 B2
(45) Date of Patent: Jun. 22, 2021

(54) GENETIC MARKERS FOR DISCRIMINATION AND DETECTION OF RED SEA BREAM IRIDOVIRUS CAUSING INFECTIOUS AQUATIC ORGANISM DISEASES, AND METHOD OF DISCRIMINATING AND DETECTING THE VIRUS USING THE SAME

(71) Applicant: National Institute of Fisheries Science, Busan (KR)

(72) Inventors: Miyoung Cho, Busan (KR); Myoung Ae Park, Busan (KR); Bo-Young Jee, Busan (KR); Seong Don Hwang, Busan (KR)

(73) Assignee: NATIONAL INSTITUTE OF FISHERIES SCIENCE, Busan (KR)

( * ) Notice: Subject to any disclaimer, the term of this patent is extended or adjusted under 35 U.S.C. 154(b) by 0 days.

(21) Appl. No.: 16/658,117

(22) Filed: Oct. 20, 2019

(65) Prior Publication Data

US 2020/0040384 A1    Feb. 6, 2020

Related U.S. Application Data

(63) Continuation of application No. 15/740,475, filed as application No. PCT/KR2016/009373 on Aug. 24, 2016, now Pat. No. 10,494,666.

(30) Foreign Application Priority Data

Jan. 15, 2016 (KR) .................... 10-2016-0005611

(51) Int. Cl.
| | |
|---|---|
| *C12Q 1/68* | (2018.01) |
| *C12Q 1/6837* | (2018.01) |
| *C12Q 1/6809* | (2018.01) |
| *C12Q 1/6897* | (2018.01) |
| *C12Q 1/70* | (2006.01) |

(52) U.S. Cl.
CPC ......... *C12Q 1/6837* (2013.01); *C12Q 1/6809* (2013.01); *C12Q 1/6897* (2013.01); *C12Q 1/705* (2013.01); *C12Q 2525/107* (2013.01)

(58) Field of Classification Search
None
See application file for complete search history.

(56) References Cited

U.S. PATENT DOCUMENTS

| | | | |
|---|---|---|---|
| 2004/0121371 A1 | 6/2004 | Andersen et al. | |
| 2018/0195114 A1 | 7/2018 | Cho et al. | |

FOREIGN PATENT DOCUMENTS

| | | | | |
|---|---|---|---|---|
| KR | 10-2008-0066301 A | 7/2008 | | |
| KR | 10-2014-0091944 A | 7/2014 | | |
| KR | 10-2015-0028063 A | 3/2015 | | |
| KR | 10-1642784 B1 | 7/2016 | | |
| KR | 101642783 B1 | * | 7/2016 | ............... C12Q 1/70 |
| KR | 101644776 B1 | * | 8/2016 | ............... C12Q 1/70 |

OTHER PUBLICATIONS

Machine Translation for KR 10-1644776; obtained from K-PION http://kposd.kipo.go.kr:8088/kiponet/up/kpion/patent/publication/selectPatentPublication.do?decorator=popupp on Dec. 9, 2020. 12 pages (Year: 2016).*
Machine Translation for KR 10-1642783; obtained from K-PION http://kposd.kipo.go.kr:8088/kiponet/up/kpion/patent/publication/selectPatentPublication.do?decorator=popup on Dec. 9, 2020. 12 pages. (Year: 2016).*
Kurita et al. Fish Pathology 33(1) 17-23, 1998. (Year: 1998).*
GenBank AB007366. Red sea bream iridovirus gene for DNA polymerase, complete cds. Jun. 10, 1998, two pages. (Year: 1998).*
Bercovier, H., et al., "Cloning of the Koi Herpesvirus (KHV) Gene Encoding Thymidine Kinase and its use for a Highly Sensitive PCR Based Diagnosis", "BMC Microbiology", Mar. 17, 2005, pp. 1-9, vol. 5, No. 13.
Genbank, "Cyprinid Herpesvirus 3 (KHV, CyHV-3) DNA, Enlarged Sphl-5 PCR Region, Genotype/Variant: A1, A2", "GenBank AB375381", Jun. 2009.
Genbank, "Cyprinid Herpesvirus 3 Isolate KHV-GZ11 Thymidine Kinase Gene, Compete cds", "GenBank JQ247183", Jan. 2013.
Kim, I.-W., et al., "Diagnosis Case of Viral Hemorrhagic Septicemia (VHS) in Adult Olive F lounder Paralichthys olivaceus", "Korean Journal of Fisheries and Aquatic Sciences", Dec. 2012, pp. 666-674 (English Abstract), vol. 45, No. 6.
Kurita, J., et al., "Molecular Epidemiology of Koi Herpesvirus", "Fish Pathology", 2009, pp. 59-66, vol. 44, No. 2.

(Continued)

*Primary Examiner* — Juliet C Switzer
(74) *Attorney, Agent, or Firm* — Hultquist, PLLC; Steven J. Hultquist

(57) ABSTRACT

Genetic markers are described for discriminating or detecting viruses causing infectious aquatic organism diseases, and a method of discriminating and detecting the viruses using the same is disclosed, in which the method includes selecting and amplifying a DNA nucleotide sequence encoding a gene specific for viral hemorrhagic septicemia virus (VHSV), red sea bream iridovirus (RSIV) or infectious spleen and kidney necrosis virus (ISKNV), which is a virus causing red sea bream iridovirus disease, or Koi herpesvirus (KHV); hybridizing a peptide nucleic acid (PNA) that specifically recognizes the amplification product; controlling the temperature of the hybridization product to obtain a temperature-dependent melting curve; and discriminating the viral type or detecting whether or not fish are infected with the viral type by analyzing the obtained melting curve to determine a melting temperature.

8 Claims, 7 Drawing Sheets
(7 of 7 Drawing Sheet(s) Filed in Color)
Specification includes a Sequence Listing.

(56) References Cited

OTHER PUBLICATIONS

Oie Aquatic Animals Commission, "Red Sea Bream Iridoviral Disease", "Manual of Diagnostic Tests for Aquatic Animals", 2009, pp. 251-261.

Petersen, K., et al., "Short PNA Molecular Beacons for Real-Time PCR Allelic Discrimination of Single Nucleotide Polymorphisms", "Molecular and Cellular Probes", 2004, pp. 117-122, vol. 18.

Pokorova, D., et al., "Tests for the Presence of Koi Herbesvirus (KHV) in Common Carp (Cyprinus Carpio Carpio) and Koi Carp (Cyprinus Carpio koi) in the Czech Republic", "Veterinami Medicina", 2007, pp. 562-568, vol. 52.

\* cited by examiner

FIG. 3

```
         10         20         30         40         50         60
 atggaaggag gaattcgtgc agcgttttca ggcctgaatg atgttaggat tgacccacc
         70         80         90        100        110        120
 ggtggagagg gacgggtact tgtacctggt gaagtggagc tcgtcgtgta tgtcggtgga
        130        140        150        160        170        180
 tttggtgagg aagataggaa ggtgattgtg gatgcactct ccgcactcgg gggacccag
        190        200        210        220        230        240
 actgtacagg cgttgtccgt gcttctctcc tatgtactcc aagggaatac acaggaggac
        250        260        270        280        290        300
 ctagaaacaa agtgcaaggt cctcacagac atgggcttca aggtgacaca ggcagccagg
        310        320        330        340        350        360
 gccacgagca tcgaggcagg aatcatgatg cccatgagag aactggccct gactgtcaat
        370        380        390        400        410        420
 gacgacaacc tcatggaaat cgttaagggg accttgatga catgctccct tctgaccaag
        430        440        450        460        470        480
 tactcggtgg acaagatgat caagtacatc accaagaaac tcggggagct ggcagacacc
        490        500        510        520        530        540
 cagggagttg gggaactgca gcacttcacc gc
```

FIG. 4

```
RSIV_OIE01      CCATTTGTGTATCTCACCACATTTATACAGTCACTGCAGTTGCCGCTAAACACTCTGGC 120
ISKNV_OIE01     CCATTTGTGTATCTCACCACATTTTCACAGTCACTGCAGTTGCCGCTCAAACACTCTGGC 93
                ************************  **************************  ****** ****

RSIV_OIE01      TCATCTATGTCATCGTAGTCGTCCATTCCGCTGCCCCCATCGTCAAGCAGTGTAGGCGGT 180
ISKNV_OIE01     TCATCTATGTCATCGTAGTCGTCCATTCCGCTGCCCCCATCGTCAAGCAGTGTAGGTGGT 153
                ********************************************************  ***

RSIV_OIE01      GGAGTAACATTATCGGTGTCTGTTGGCAGCTCACATGAGACACCTACACAAGGCTGACTG 240
ISKNV_OIE01     GGAGTAACGTCATCGGTGTCTGTCGGCAGCTCACATGAGACGCCTACACAAGGCTGACTG 213
                ********  * ***********  ****************  ****************

RSIV_OIE01      TCAGATGAGATGCGGCTGGCGTGGCATGTGACGGTCTGCACAGGGTGAGGTTTCAGCTTG 300
ISKNV_OIE01     TCAGATGAGATGCGGCTGGCGTGGCATGTGACGCTCTGCACAGGGTGAGGTTTCAGCTTG 273
                *********************************  *************************

RSIV_OIE01      ATGACAGACAAGATGGTACCGTCATACAGCACCACTCCATGCTTCAGGACTTCACTGCTG 360
ISKNV_OIE01     ATGACAGACACAATGGTACCATCATACAGCACCACTCCATGTTTCAGGACTTCGCTGCTG 333
                **********  *******  ****************** *********** ********

RSIV_OIE01      TTGCGGCCTACATGGACCACCTCGCCATGTACAACATGCTCCGCCAAGAGGCTGTTGCTG 420
ISKNV_OIE01     TTGCGGCCTACATGTACCACCTGGCCATGTACAACATGCTCTGCCAACAGGCTGTTGCTG 393
                **************  ******  *****************  ****  ***********

RSIV_OIE01      TCGCTTGACCAAACAATCTTCACATCCGTCTCTCGAGGTACCCCGCAGCTGAGGGTGGTC 480
ISKNV_OIE01     TCGCTTGCCCAAACAATCTTCACATCAGTCTCTCGAGGTACCCCGCAGCTGAGGGTGGTC 453
                *******  ****************** *************************************

RSIV_OIE01      GTCTGGTTGTCGATTTCCAGGTTATAGAAGGTGGTGGCGTGAGTACACGCCACAGTCAGC 540
ISKNV_OIE01     GTCTGGTTGTCAATTTCCAGGTTATAGAAGGTGGTGGCGTGGCTATATGCCACAGTCAGC 513
                *********** ****************************  ** * ************

RSIV_OIE01      AACAGAAGAAGTAGCAGGGTCGCCATTGCTCATGTAGCTATGATTCACAGTAGTCACCTA 600
ISKNV_OIE01     AACACAAGAAGTAGCAGAGTCGCCATTGGTCCGCTAGGTATGTTTTCAGTGGTCATATA 573
                ****  *********** *********  **   *** **** ** **** ****  **

RSIV_OIE01      TGACATGAGGATATTCAAAATTTTTATACAAGTAAAAGATGTTCACTGTGCTTGAGATAG 660
ISKNV_OIE01     TGACATGAGGATATTCAAAATTTTTATACAAGTAAAAGATGTTCACTGTGCTTGAGATAG 633
                **********************************************************

RSIV_OIE01      GAGATGTTTGGTGCTAGTGTCGCGTGACGACATACGTGTGATGTACAACCGTGACCCGG 720
ISKNV_OIE01     GAGACGTTTGGTGCTAGTGTCGCGTGACAACATACGCGTGATGTACAACCGCGACCCGG 693
                ****  *********************** ******  ************** ******
```

FIG. 5

```
RSIV_Polymerase     CGGGGGCAATGACGACTACATACTGCGGCCGCAAGCTGATTGAGAAAGCCGCTCATCTCC 60
ISKNV_Polymerase    CGGGGGCAATGACGCGATGTACTGTGGCCGCAAGCTGATTGAGAAGGCCGCTCATCTCC 60
                    ****************  **  ****  *********************** ***********

RSIV_Polymerase     TCAAGACGGTGGTGGGCGCTACCATTGTGTACGGCGACACCGACTCATGCTACATACAGC 120
ISKNV_Polymerase    TTAAGACGGTGGTGGGCGCTACCATTGTGTACGGCGACACCGACTCGTGCTACATACAGC 120
                    * ********************************************** ************

RSIV_Polymerase     TGGGCCACGACCGCGCATCACTCGATGAACTGTGGCAGATGGCTGTAAACGCCAGTGACA 180
ISKNV_Polymerase    TGGGCCACGACCGCGCATCACTCGATGAACTGTGGCAGATGGCCGTGAACGCCAGCGACA 180
                    ******************************************* ** ******** ****

RSIV_Polymerase     CTGTGTCGGCTTCTTTGAGCGCCCGGTGCGCCTCGAGTTTGAGCAGTGCATCTACACCA 240
ISKNV_Polymerase    CCGTGTCGGCCTTCTTTGAGCGCCCGGTGCGCCTCGAGTTTGAGCAGTGCATCTACACCA 240
                    * ******** *************************************************

RSIV_Polymerase     AGTTCATCATCTTCACCAAGAAACGTTATGTGTACAGGGCATTCACACGCGACGGCAAGC 300
ISKNV_Polymerase    AGTTTATCATCTTCACCAAGAAACGTTATGTGTACAGGGCATTCACACGCGACGGCAAGC 300
                    **** *******************************************************

RSIV_Polymerase     AGCGAACAGGCAGCAAGGGTGTCATGTTGTCCAGACGTGACAGCGCCATGTGTGCCAGAA 360
ISKNV_Polymerase    AGCGAACAGGCAGCAAGGGTGTGATGCTGTCCAGACGCGACAGCGCCATGTGTGCCAGAA 360
                    ********************** *** ********** **********************

RSIV_Polymerase     ACACGTATGCAGCAATCATGAGTGCAATCCTTGAGGGTCTGCAGATGTGCCATTCATTG 420
ISKNV_Polymerase    ACACGTATGCGGCAATCATGAACACGATCCTTGAGGGATCTGCAGATGTGCCGTTCATTG 420
                    ********** **********  * *********** ************** *******

RSIV_Polymerase     CTGTGCGCATGATGCACGACATGATGATACCGGGAGCGCTTCAAGATGACGACTTTGTGC 480
ISKNV_Polymerase    CCGCGTGCATGATGCACGACATGATGATACCGGGAGCGCTTCAAGACGACGACTTTGTGC 480
                    * *  * *************************************** *************

RSIV_Polymerase     TGACAAAGAGTGTGCAGGATATCGGCAATGGGGACGACAACAACCACGGCTCGTACAAAG 540
ISKNV_Polymerase    TGACAAAGAGTGTGCAGGACATTGGCAATGGGGACGATAACAACCAGGGCTCGTACAAAG 540
                    ******************* ** ************** ******* **************

RSIV_Polymerase     TTAGGAATCCACAAAGGCGTAGGCGG 567
ISKNV_Polymerase    TTAGGAATCCACAGAAGGCGTAGGCGG 567
                    * *********** *** *********
```

FIG. 6

```
        10         20         30         40         50         60
GGGTTACCTG TACGAGGTGA TGCAGCGTCT GGAGGAATAC GACGCCGTGG CCGTCGACGA
        70         80         90        100        110        120
GGGACAGTTC TTCCCCGACC TCTACGAGGG AGTCGTGCAG CTGCTGACCG CGGGCAAGTA
       130        140        150        160        170        180
CGTGATCGTG GCGGCGCTGG ACGGGACTT  TATGCAGCAG CCCTTCAAGC AGGTGACGGC
       190        200        210        220        230        240
GTTGGTGCCC ATGGCGGACA AGCTGGACAA GCTGACGGCG GTGTGCATGA AGTGCAAGAT
       250        260        270        280        290        300
GCGCGACGCA CCCTTCACCG TCAGAATCTC TCAGGGCACG GACCTGGTCC AGGTTGGAGG
       310        320        330        340        350        360
CGCCGAGTCT TACCAGGCGG TGTGTCGTCC CTGTCTCACG GGGTTCAGGA TGGCCCAGTA
       370        380        390        400        410        420
CGAGCTGTAC GGTCCGCCGC CTCCTCCTCC TGCGCATAAT CTACTGGGTG
```

FIG. 7

```
        10         20         30         40         50         60
GACACCACAT CTGCAAGGAG TGCTCGAACA AGCTGCCCGC TCAGAGGGAC AATCTCAGCA
        70         80         90        100        110        120
ACACCTACCA CAGCACGTGC CCGCAGTGCA GGGACCCGAG CATCGTGGGG TTCCAGACCA
       130        140        150        160        170        180
TGGACCTCGC ATACGCCGTC GAGGACCGCT ACAAGAGCCT CTTCAAGCTG ACGCCGCAAC
       190        200        210        220        230        240
AGTCGCAGTC GTTCAAGAAG CACATACTGC GGTGAGACGA CGGCGAGGAC CCGCAGCGCA
       250        260        270        280        290        300
CGGGAAACCT CCGCAACCTC CCAACATTGA TGCGACCATT GTAACATGTG TC
```

FIG. 8

| Product | VHSV | RSIV/ISKNV-1 | RSIV/ISKNV-4 | KHV-TK | KHV-GS |
|---------|------|--------------|--------------|--------|--------|
| Tm | 64-66°C | 64-66°C | 65-67°C | 59-61°C | 61-63°C |

SEQUENCE LISTING

<160> NUMBER OF SEQ ID NOS: 22

<210> SEQ ID NO 1
<211> LENGTH: 13
<212> TYPE: DNA
<213> ORGANISM: Artificial Sequence
<220> FEATURE:
<223> OTHER INFORMATION: PNA 1

<400> SEQUENCE: 1
tgaagcccat gtc                                                        13

<210> SEQ ID NO 2
<211> LENGTH: 17
<212> TYPE: DNA
<213> ORGANISM: Artificial Sequence
<220> FEATURE:
<223> OTHER INFORMATION: PNA 2

<400> SEQUENCE: 2
ccatgtacaa catgctc                                                    17

<210> SEQ ID NO 3
<211> LENGTH: 14
<212> TYPE: DNA
<213> ORGANISM: Artificial Sequence
<220> FEATURE:
<223> OTHER INFORMATION: PNA 3

<400> SEQUENCE: 3
gatgatgaac ttgg                                                14

<210> SEQ ID NO 4
<211> LENGTH: 13
<212> TYPE: DNA
<213> ORGANISM: Artificial Sequence
<220> FEATURE:
<223> OTHER INFORMATION: PNA 4

<400> SEQUENCE: 4
gttcttcccc gac                                                 13

<210> SEQ ID NO 5
<211> LENGTH: 13
<212> TYPE: DNA
<213> ORGANISM: Artificial Sequence
<220> FEATURE:
<223> OTHER INFORMATION: PNA 5

<400> SEQUENCE: 5
tctcagcaac acc                                                 13

<210> SEQ ID NO 6
<211> LENGTH: 24
<212> TYPE: DNA
<213> ORGANISM: Artificial Sequence
<220> FEATURE:
<223> OTHER INFORMATION: Primer 1

<400> SEQUENCE: 6
atggaaggag gaattcgtga agcg                                     24

<210> SEQ ID NO 7
<211> LENGTH: 20
<212> TYPE: DNA
<213> ORGANISM: Artificial Sequence
<220> FEATURE:
<223> OTHER INFORMATION: Primer 2

<400> SEQUENCE: 7
gcaccaacac atctcctatc                                          20

<210> SEQ ID NO 8
<211> LENGTH: 20
<212> TYPE: DNA
<213> ORGANISM: Artificial Sequence
<220> FEATURE:
<223> OTHER INFORMATION: Primer 3

<400> SEQUENCE: 8
cgggggcaat gacgactaca                                          20

<210> SEQ ID NO 9
<211> LENGTH: 17
<212> TYPE: DNA
<213> ORGANISM: Artificial Sequence
<220> FEATURE:
<223> OTHER INFORMATION: Primer 4

<400> SEQUENCE: 9
cacccagtag attatgc                                             17

<210> SEQ ID NO 10

```
<211> LENGTH: 21
<212> TYPE: DNA
<213> ORGANISM: Artificial Sequence
<220> FEATURE:
<223> OTHER INFORMATION: Primer 5

<400> SEQUENCE: 10
gacacatgtt acaatggtcg c                                              21

<210> SEQ ID NO 11
<211> LENGTH: 13
<212> TYPE: DNA
<213> ORGANISM: Artificial Sequence
<220> FEATURE:
<223> OTHER INFORMATION: VM 1

<400> SEQUENCE: 11
gacatgggct tca                                                       13

<210> SEQ ID NO 12
<211> LENGTH: 17
<212> TYPE: DNA
<213> ORGANISM: Artificial Sequence
<220> FEATURE:
<223> OTHER INFORMATION: VM 2

<400> SEQUENCE: 12
ccatgtacaa catgctc                                                   17

<210> SEQ ID NO 13
<211> LENGTH: 14
<212> TYPE: DNA
<213> ORGANISM: Artificial Sequence
<220> FEATURE:
<223> OTHER INFORMATION: VM 3

<400> SEQUENCE: 13
ccaagttcat catc                                                      14

<210> SEQ ID NO 14
<211> LENGTH: 13
<212> TYPE: DNA
<213> ORGANISM: Artificial Sequence
<220> FEATURE:
<223> OTHER INFORMATION: VM 4

<400> SEQUENCE: 14
gttcttcccc gac                                                       13

<210> SEQ ID NO 15
<211> LENGTH: 13
<212> TYPE: DNA
<213> ORGANISM: Artificial Sequence
<220> FEATURE:
<223> OTHER INFORMATION: VM 5

<400> SEQUENCE: 15
tctcagcaac acc                                                       13

<210> SEQ ID NO 16
<211> LENGTH: 512
<212> TYPE: DNA
<213> ORGANISM: Artificial Sequence
<220> FEATURE:
<223> OTHER INFORMATION: VSHV

<400> SEQUENCE: 16
```

-continued

```
atggaaggag gaattcgtgc agcgttttca ggcctgaatg atgttaggat tgaccccacc      60
ggtggagagg gacgggtact tgtacctggt gaagtggagc tcgtcgtgta tgtcggtgga     120
tttggtgagg aagataggaa ggtgattgtg gatgcactct ccgcactcgg gggaccccag     180
actgtacagg cgttgtccgt gcttctctcc tatgtactcc aagggaatac acaggaggac     240
ctagaaacaa agtgcaaggt cctcacagac atgggcttca aggtgacaca ggcagccagg     300
gccacgagca tcgaggcagg aatcatgatg cccatgagag aactggccct gactgtcaat     360
gacgacaacc tcatggaaat cgttaagggg accttgatga catgctccct tctgaccaag     420
tactcggtgg acaagatgat caagtacatc accaagaaac tcggggagct ggcagacacc     480
cagggagttg ggaactgca gcacttcacc gc                                  512
```

```
<210> SEQ ID NO 17
<211> LENGTH: 750
<212> TYPE: DNA
<213> ORGANISM: Artificial Sequence
<220> FEATURE:
<223> OTHER INFORMATION: RSIV_OIE01

<400> SEQUENCE: 17
agcatattgt agggcatctc accggggaca cacagcttat catccagaca ctccaaagag      60
ccatttgtgt atctcaccac atttatacag tcactgcagt tgccgctcaa acactctggc     120
tcatctatgt catcgtagtc gtccattccg ctgcccccat cgtcaagcag tgtaggcggt     180
ggagtaacat tatcggtgtc tgttggcagc tcacatgaga cacctacaca aggctgactg     240
tcagatgaga tgcggctggc gtggcatgtg acggtctgca cagggtgagg tttcagcttg     300
atgacagaca agatggtacc gtcatacagc accactccat gcttcaggac ttcactgctg     360
ttgcggccta catggaccac ctcgccatgt acaacatgct ccgccaagag gctgttgctg     420
tcgcttgacc aaacaatctt cacatccgtc tctcgaggta ccccgcagct gagggtggtc     480
gtctggttgt cgatttccag gttatagaag gtggtggcgt gagtacacgc cacagtcagc     540
aacagaagaa gtagcagggt cgccattgct catgtagcta tgattcacag tagtcaccta     600
tgacatgagg atattcaaaa tttttataca agtaaaagat gttcactgtg cttgagatag     660
gagatgtgtt ggtgctagtg tcgcgtgacg acatacgtgt gatgtacaac cgtgacccgg     720
gacaatctgt ggcgttaact aataccacca                                      750
```

```
<210> SEQ ID NO 18
<211> LENGTH: 750
<212> TYPE: DNA
<213> ORGANISM: Artificial Sequence
<220> FEATURE:
<223> OTHER INFORMATION: ISKNV_OIE01

<400> SEQUENCE: 18
ccggggacac actcatccag acactccaaa gagccatttg tgtatctcac cacattttca      60
cagtcactgc agttgccgct caaacactct ggctcatcta tgtcatcgta gtcgtccatt     120
ccgctgcccc catcgtcaag cagtgtaggt ggtggagtaa cgtcatcggt gtctgtcggc     180
agctcacatg agacgcctac acaaggctga ctgtcagatg agatgcggct ggcgtggcat     240
gtgacgctct gcacagggtg aggtttcagc ttgatgacag acacaatggt accatcatac     300
agcaccactc catgtttcag gacttcgctg ctgttgcggc ctacatgtac cacctcgcca     360
tgtacaacat gctctgccaa caggctgttg ctgtcgcttg cccaaacaat cttcacatca     420
```

```
gtctctcgag gtaccccgca gctgagggtg gtcgtctggt tgtcaatttc caggttatag    480
aaggtggtgg cgtggctata tgccacagtc agcaacacaa gaagtagcag agtcgccatt    540
ggtccgctag gtatgttttc cagtggtcat atatgacatg aggatattca aaattttat    600 acaagtaaaa gatgttcact gtgcttgaga taggagacgt gttggtgcta gtgtcgcgtg    660
acaacatacg cgtgatgtac aaccgcgacc cggggcaagc cgtggcgtta ataatacca    720 cccaagggtg cgtcacggtc acggcggtgc                                    750
```

```
<210> SEQ ID NO 19
<211> LENGTH: 567
<212> TYPE: DNA
<213> ORGANISM: Artificial Sequence
<220> FEATURE:
<223> OTHER INFORMATION: RSIV_Polymerase

<400> SEQUENCE: 19
cgggggcaat gacgactaca tactgcggcc gcaagctgat tgagaaagcc gctcatctcc    60
tcaagacggt ggtgggcgct accattgtgt acggcgacac cgactcatgc tacatacagc   120
tgggccacga ccgcgcatca ctcgatgaac tgtggcagat ggctgtaaac gccagtgaca   180
ctgtgtcggc cttctttgag cgcccggtgc gcctcgagtt tgagcagtgc atctacacca   240
agttcatcat cttcaccaag aaacgttatg tgtacagggc attcacacgc gacggcaagc   300
agcgaacagg cagcaagggt gtcatgttgt ccagacgtga cagcgccatg tgtgccagaa   360
acacgtatgc agcaatcatg agtgcaatcc ttgagggtc tgcagatgtg ccattcattg    420
ctgtgcgcat gatgcacgac atgatgatac cgggagcgct tcaagatgac gactttgtgc   480
tgacaaagag tgtgcaggat atcggcaatg gggacgacaa caaccacggc tcgtacaaag   540
ttaggaatcc acaaaaggca caggcgg                                       567
```

```
<210> SEQ ID NO 20
<211> LENGTH: 567
<212> TYPE: DNA
<213> ORGANISM: Artificial Sequence
<220> FEATURE:
<223> OTHER INFORMATION: ISKNV_Polymerase

<400> SEQUENCE: 20
cgggggcaat gacgacgacg tactgtggcc gcaagctgat tgagaaggcc gctcatctcc    60
ttaagacggt ggtgggcgct accattgtgt acggcgacac cgactcgtgc tacatacagc   120
tgggccacga ccgcgcatca ctcgatgaac tgtggcagat ggccgtgaac gccagcgaca   180
ccgtgtcggc cttctttgag cgcccggtgc gcctcgagtt tgagcagtgc atctacacca   240
agtttatcat cttcaccaag aaacgttatg tgtacagggc attcacacgc gacggcaagc   300
agcgaacagg cagcaagggt gtgatgctgt ccagacgcga cagcgccatg tgtgccagaa   360
acacgtatgc ggcaatcatg aacacgatcc ttgagggatc tgcagatgtg ccgttcattg   420
ccgcgtgcat gatgcacgac atgatgatac cgggagcgct tcaagacgac gactttgtgc   480
tgacaaagag tgtgcaggac attggcaatg gggacgataa caaccagggc tcgtacaaag   540
tcaggaatcc acagaaggcg caggcgg                                       567
```

```
<210> SEQ ID NO 21
<211> LENGTH: 410
<212> TYPE: DNA
<213> ORGANISM: Artificial Sequence
<220> FEATURE:
<223> OTHER INFORMATION: KHV TK
```

```
<400> SEQUENCE: 21
gggttacctg tacgaggtga tgcagcgtct ggaggaatac gacgccgtgg ccgtcgacga      60
gggacagttc ttccccgacc tctacgaggg agtcgtgcag ctgctgaccg cgggcaagta     120
cgtgatcgtg gcggcgctgg acggggactt tatgcagcag cccttcaagc aggtgacggc     180
gttggtgccc atggcggaca agctggacaa gctgacggcg gtgtgcatga agtgcaagat     240
gcgcgacgca cccttcaccg tcagaatctc tcagggcacg gacctggtcc aggttggagg     300
cgccgagtct taccaggcgg tgtgtcgtcc ctgtctcacg gggttcagga tggcccagta     360
cgagctgtac ggtccgccgc ctcctcctcc tgcgcataat ctactgggtg                410

<210> SEQ ID NO 22
<211> LENGTH: 292
<212> TYPE: DNA
<213> ORGANISM: Artificial Sequence
<220> FEATURE:
<223> OTHER INFORMATION: KHV

<400> SEQUENCE: 22
gacaccacat ctgcaaggag tgctcgaaca agctgcccgc tcagagggac aatctcagca      60
acacctacca cagcacgtgc ccgcagtgca gggacccgag catcgtgggg ttccagacca     120
tggacctcgc atacgccgtc gaggaccgct acaagagcct cttcaagctg acgccgcaac     180
agtcgcagtc gttcaagaag cacatactgc ggtgagacga cggcgaggac ccgcagcgca     240
cgggaaacct ccgcaacctc ccaacattga tgcgaccatt gtaacatgtg tc             292
```

GENETIC MARKERS FOR DISCRIMINATION AND DETECTION OF RED SEA BREAM IRIDOVIRUS CAUSING INFECTIOUS AQUATIC ORGANISM DISEASES, AND METHOD OF DISCRIMINATING AND DETECTING THE VIRUS USING THE SAME

CROSS-REFERENCE TO RELATED APPLICATIONS

This application is a continuation under 35 U.S.C. § 120 of U.S. patent application Ser. No. 15/740,475 filed Dec. 28, 2017, which in turn is a U.S. national phase under the provisions of 35 U.S.C. § 371 of International Patent Application No. PCT/KR2016/009373 filed Aug. 24, 2016, which in turn claims priority under 35 U.S.C. § 119 of Korean Patent Application No. 10-2016-0005611 filed Jan. 15, 2016. The disclosures of U.S. patent application Ser. No. 15/740,475, International Patent Application No. PCT/KR2016/009373, and 35 U.S.C. § 119 of Korean Patent Application No. 10-2016-0005611 are hereby incorporated herein by reference in their respective entireties, for all purposes.

TECHNICAL FIELD

The present invention relates to genetic markers for discrimination and detection of viruses causing infectious aquatic organism diseases, and a method of discriminating and detecting the viruses using the same. More specifically, the present invention relates to a method for discriminating or detecting viruses causing infectious aquatic organism diseases, the method comprising: selecting and amplifying a DNA nucleotide sequence encoding a gene specific for viral hemorrhagic septicemia virus (VHSV), red sea bream iridovirus (RSIV) or infectious spleen and kidney necrosis virus (ISKNV), which is a virus causing red sea bream iridovirus disease, or Koi herpesvirus (KHV); hybridizing a peptide nucleic acid (PNA) that specifically recognizes the amplification product; controlling the temperature of the hybridization product to obtain a temperature-dependent melting curve; and discriminating the viral type or detecting whether or not fish would be infected with the viral type by analyzing the obtained melting curve to determine a melting temperature.

BACKGROUND ART

Among recent methods for diagnosis of infectious diseases, diagnostic methods and kits based on molecular diagnosis have been developed. Among these methods, a method has been mainly used, which comprises performing general polymerase chain reaction (PCR) to obtain an amplification product, and then either analyzing the amplification product by electrophoresis, or analyzing the amplification by real-time PCR using a fluorescent probe or SYBR green.

Particularly, among infectious aquatic organism diseases, viral hemorrhagic septicemia virus (VHSV), red sea bream iridovirus (RSIV)/infectious spleen and kidney necrosis virus (ISKNV), or Koi herpesvirus (KHV), is classified as a nationally notifiable infectious disease. For the purpose of detection of this virus, according to the standards set forth in the Aquatic Animal Health Code of the World Organization for Animal Health (OIE), conventional PCR is performed to obtain an amplification product, and the amplification product is analyzed by electrophoresis, after which the amplification product is cloned, and the nucleotide sequence of the purified plasmid DNA is analyzed by a process such as Sanger sequencing. Thus, there are disadvantages in that the procedures are complex and analysis for disease diagnosis is time-consuming.

For molecular diagnosis of the fish virus VHSV, various techniques for genetic diagnosis have been developed, including RT-PCR and real-time RT-PCR, which enables diagnosis with high accuracy and sensitivity within a short time. For VHSV diagnosis, a conventional RT-PCR process composed of one step or two steps is used according to the OIE standards. Particularly, as genetic variants of the virus have recently been cyclically found in North America, Asia, Europe and Atlantic areas, studies on the epidemiological dynamics of the causative virus have been conducted, and genotype analysis based on sequencing of an amplification product, which is performed after performing PCR according to the OIE standards in order to obtain accurate results in molecular diagnosis, has been of increasing importance. In recent years, techniques such as LAMP (loop-mediated isothermal amplification) for simple genotype analysis have been developed, but these techniques are not recommended by the OIE, since there is a limit to detection of viruses having various genotypes.

For the purpose of detection of RSIV or ISKNV, which is a virus causing red sea bream iridovirus disease, a staining technique based on a tissue smear sample, and serological diagnostic methods such as IFAT based on MAb, are used. For molecular diagnosis, conventional PCR is performed using two kinds of primers according to the OIE standards. The diagnostic methods recommended by the OIE are methods for diagnosis of red sea bream iridovirus disease (RSIVD). Among them, the use of the "OIE protocol 1 (OIE 1)" PCR method makes it possible to diagnose the red sea bream iridovirus disease without discrimination between RSIV and ISKNV, and the use of the "OIE protocol 2 (OIE 4)" PCR method makes it possible to discriminate between RSIV and ISKNV, which are viruses causing the red sea bream iridovirus disease, by specifically amplifying only RSIV without amplifying ISKNV. Thus, there is a disadvantage in that two conventional PCR steps according to the OIE standards should be performed for diagnosis of red sea bream iridovirus disease and for accurate identification of a virus causing the disease.

For the purpose of molecular diagnosis of Koi herpesvirus (KHV), two conventional PCR methods (OIE, 2014) found to be most sensitive for KHV diagnosis among a variety of disclosed PCR methods are performed. The first method is a method using "Bercovier TK primers" developed by Bercovier et al. in 2005, and the second method is a method developed by Yuasa et al (Gray Sph primers/Yuasa modification). Although diagnostic methods such as real-time PCR, which have higher sensitivity than conventional PCR methods, are frequently performed in many diagnostic laboratories, the above-mentioned two PCR methods are most frequently performed in order to avoid contamination during sample preparation and PCR processes. At present, for diagnosis and identification of the nationally notifiable infectious diseases, conventional PCR methods are used as standard diagnostic methods recommended by nations.

Analysis of a PCR amplification product by electrophoresis according to the OIE standards cannot be objectively achieved (gray zone), or a verification step is performed, which includes cloning a faint PCR amplification product using a cloning vector and then re-confirming the nucleotide sequence of the amplification product by sequencing. This verification step is performed by analyzing the sequence of a non-specific PCR band, and has problems in that analytical procedures are complex and time-consuming. Particularly, when conventional PCR (before determination by sequencing) indicates that an amplification product is positive, the amplification product is recognized to have the risk of causing infectious diseases of aquatic organisms, and thus preventive measures are taken. However, when sequencing performed later indicates that the PCR result is false-positive, the reliability of the testing laboratory can be lowered, and damage to fishery cooperatives may also occur. For this reason, there is an urgent need for improved methods that diagnose nationally notifiable infectious diseases in a rapid and accurate manner.

Under this technical background, the present inventors have made extensive efforts to develop a method that discriminates fish disease-causing viruses by determining whether or not a PCR product for discrimination or detection of VHSV, RSIV/ISKNV or KHV, which is a virus causing infectious aquatic organism diseases, would be specifically/nonspecifically amplified, without or before performing a sequencing step, and that detects an individual (e.g., fish) infected with the causative virus. As a result, the present inventors have identified genetic markers for discrimination and/or detection of the type of VHSV, RSIV/ISKNV or KHV, which is a virus causing fish diseases, and have found that when peptide nucleic acids and primers specific for the genetic markers are used to obtain amplification and melting curves having different fluorescence intensities depending on the type of virus, fish disease-causing virus can be discriminated in a simple, rapid and accurate manner, thereby completing the present invention.

DISCLOSURE OF INVENTION

Technical Problem

It is an object of the present invention to provide a genetic marker, a primer and a PNA probe for discrimination or detection of VHSV, RSIV/ISKNV or KHV, which is a virus causing infectious aquatic organism disease.

Another object of the present invention is to provide a composition and a kit for discrimination or detection of VHSV, RSIV/ISKNV or KHV, which comprises the above-described primer and the above-described PNA probe.

Another object of the present invention is to provide a method comprising: producing a single-strand genetic marker sequence fragment using the above-described primer; hybridizing the above-described PNA probe to the produced genetic marker sequence fragment; and obtaining a Tm value resulting from the hybridization of the PNA probe, thereby determining the type of VHSV, RSIV/ISKNV or KHV, or detecting whether or not an individual would be infected with the fish disease-causing virus.

Technical Solution

To achieve the above object, the present invention provides a genetic marker for discrimination or detection of viral hemorrhagic septicemia virus (VHSV), which is a virus causing infectious aquatic organism disease, in which the genetic marker is represented by a nucleotide sequence of SEQ ID NO: 11.

The present invention also provides a genetic marker for discrimination or detection of Koi herpesvirus (KHV), which is a virus causing infectious aquatic organism disease, in which the genetic marker is represented by a nucleotide sequence of SEQ ID NO: 14 or SEQ ID NO: 15.

The present invention also provides a primer for discrimination or detection of viral hemorrhagic septicemia virus (VHSV), which is a virus causing infectious aquatic organism disease, in which the primer is represented by a nucleotide sequence of SEQ ID NO: 6.

The present invention also provides a primer for discrimination or detection of red sea bream iridovirus (RSIV) or infectious spleen and kidney necrosis virus (ISKNV), which is a virus causing infectious aquatic organism disease, in which the primer is represented by a nucleotide sequence of SEQ ID NO: 7.

The present invention also provides a primer for discrimination or detection of red sea bream iridovirus (RSIV), which is a virus causing infectious aquatic organism disease, in which the primer is represented by a nucleotide sequence of SEQ ID NO: 8.

The present invention also provides a primer for discrimination or detection of Koi herpesvirus (KHV), which is a virus causing infectious aquatic organism disease, in which the primer is represented by a nucleotide sequence of SEQ ID NO: 9 or of SEQ ID NO: 10.

The present invention also provides a PNA probe for discrimination or detection of viral hemorrhagic septicemia virus (VHSV), which is a virus causing infectious aquatic organism disease, in which the PNA probe is represented by a nucleotide sequence of SEQ ID NO: 1.

The present invention also provides a PNA probe for discrimination or detection of Koi herpesvirus (KHV), which is a virus causing infectious aquatic organism disease, in which the PNA probe is represented by a nucleotide sequence of SEQ ID NO: 4 or of SEQ ID NO: 5.

The present invention also provides a composition and a kit for discrimination or detection of a virus causing infectious aquatic organism disease, which comprises the above-described primer and the above-described PNA probe.

The present invention also provides a method for discrimination or detection of a virus causing infectious aquatic organism disease, comprising the steps of:

(a) extracting a target nucleic acid from a sample;

(b) amplifying a genetic marker nucleotide sequence for an infectious aquatic organism disease-causing virus, contained in the target nucleic acid, by use of a conventional primer pair;

(c) producing a single-strand genetic marker sequence fragment using the amplified genetic marker nucleotide sequence as a template and the above-described primer;

(d) hybridizing the above-described PNA probe to the produced single-strand genetic marker sequence fragment;

(e) obtaining a temperature-dependent melting curve while increasing the temperature of a PNA probe-hybridized product resulting from step (d); and (f) discriminating the viral type of the infectious aquatic organism disease-causing virus or detecting whether or not fish would be infected with the viral type by analyzing the melting curve obtained in step (e) to determine a melting temperature.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3 is a gene position view illustrating nucleotide sequence regions included in a primer and a peptide nucleic acid probe in an amplification product obtained by the PCR method for detection of VHSV according to the OIE standards (SEQ ID NO: 16).

FIG. 4 is a gene position view illustrating nucleotide sequence regions included in a primer and a peptide nucleic acid probe in an amplification product obtained by the "PCR protocol 1 (OIE 1)" method for detection of RSIV/ISKNV according to the OIE standard (SEQ ID NOS: 17 and 18).

FIG. 5 is a gene position view illustrating nucleotide sequence regions included in a primer and a peptide nucleic acid probe in an amplification product obtained by the "PCR protocol 2 (OIE 4)" method for detection of RSIV according to the OIE standards (SEQ ID NOS: 19 and 20).

FIG. 6 is a gene position view illustrating nucleotide sequence regions included in a primer and a peptide nucleic acid probe in an amplification product obtained by the "PCR (Bercoiver TK)" method for detection of KHV according to the OIE standards (SEQ ID NO: 21).

FIG. 7 is a gene position view illustrating nucleotide sequence regions included in a primer and a peptide nucleic acid probe in an amplification product obtained by the "PCR (Gray SpH)" method for detection of KHV according to the OIE standards (SEQ ID NO: 22).

FIG. 8 shows amplification curve and melting curve graphs obtained according to virus detection methods using the primers and peptide nucleic acid probes shown in FIGS. 1 to 7.

BEST MODE FOR CARRYING OUT THE INVENTION

Figure 1:
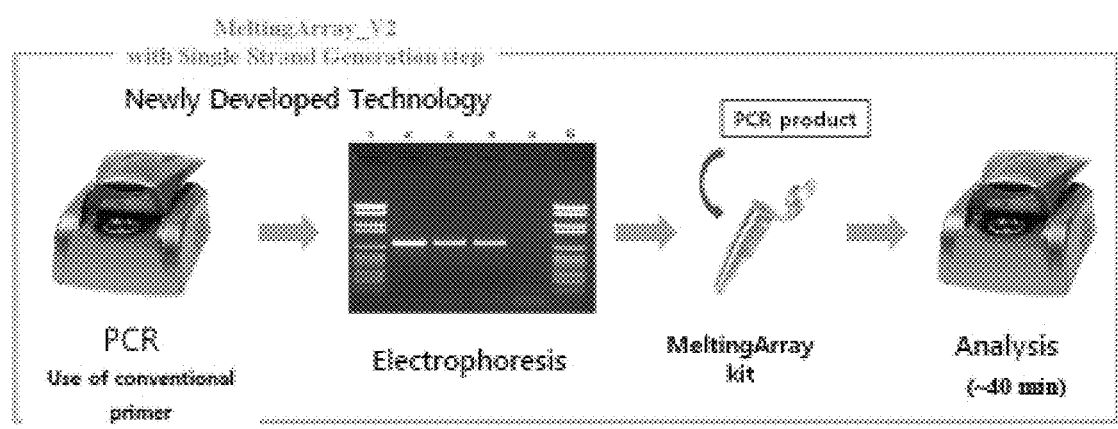
FIG. 1 is a conceptual view showing the technical characteristics of a step of obtaining an amplification curve for identifying the type of virus or detecting whether or not an individual would be infected with the viral type, in a MeltingArray for verification of a PCR amplification product.

Unless defined otherwise, all technical and scientific terms used herein have the same meaning as commonly understood by one of ordinary skill in the art to which the invention pertains. Generally, the nomenclature used herein and the experiment methods, which will be described below, are those well known and commonly employed in the art.

In an example of the present invention, it was attempted to develop a method that identifies VHSV, RSIV/ISKNV or KHV, which is an infectious aquatic organism disease-causing virus set forth in the Aquatic Animal Health Code of the World Organization for Animal Health (OIE), by determining whether or not a PCR amplification product for a genetic marker specific for the disease-causing virus would be specifically/nonspecifically amplified, without or before a sequencing step, and that detects an individual (e.g., fish) infected with the disease-causing virus. As a result, using a marker having a specific nucleotide sequence depending the type of virus and a primer and peptide nucleic acid probe (PNA probe) for discrimination of the type of virus which corresponds to the marker, viruses causing infectious aquatic organism diseases could be detected, and each virus causing infectious aquatic organism diseases could be discriminated/detected.

More specifically, the use of a composition or a kit (including a MeltingArray), which comprises the following components (1) and (2) making it possible to discriminate/detect each type of the disease-causing virus, made it possible to detect a virus causing infectious aquatic organism disease and discriminate each type of the virus causing infectious aquatic organism disease:

(1) an oligomer mixture comprising each of PNA probes (SEQ ID NOs: 1 to 5) for detection and one or more of primers (SEQ ID NOs: 6 to 10), which are specific for VHSV, RSIV/ISKNV, RSIV, and KHV, respectively; and (2) a single-strand generation buffer (SSG buffer) which is used to generate a single-strand DNA using as a template a PCR amplification product produced using the primer and to hybridize the PNA probe to the single-strand DNA.

Herein, the composition or the kit (including MeltingArray) comprises one or more of the following components (1) to (5) making it possible to discriminate/detect each type of the virus causing infectious aquatic organism disease:

(1) an oligomer mixture for detecting a PCR product for identification of VHSV, in which the oligomer mixture comprises a PNA probe (SEQ ID NO: 1) and a primer (SEQ ID NO: 6);

(2) an oligomer mixture for detecting a "PCR protocol 1 (OIE 1)" product for identification of RSIV/ISKNV, in which the oligomer mixture comprises a PNA probe (SEQ ID NO: 2) and a primer (SEQ ID NO: 7);

(3) an oligomer mixture for detecting a "PCR protocol 2 (OIE 4)" product for identification of RSIV, in which the oligomer mixture comprises a PNA probe (SEQ ID NO: 3) and a primer (SEQ ID NO: 8);

(4) an oligomer mixture for detecting a "PCR (Bercoiver TK)" product for identification of KHV, in which the oligomer mixture comprises a PNA probe (SEQ ID NO: 4) and a primer (SEQ ID NO: 9); and (5) an oligomer mixture for detecting a "PCR (Gray Sph)" product for identification of KHV, in which the oligomer mixture comprises a PNA probe (SEQ ID NO: 5) and a primer (SEQ ID NO: 10).

Therefore, in one aspect, the present invention is directed to a genetic marker for discrimination or detection of viral hemorrhagic septicemia virus (VHSV), which is a virus causing infectious aquatic organism disease, in which the genetic marker is represented by SEQ ID NO: 11.

In another aspect, the present invention is directed to a genetic marker for discrimination or detection of red sea bream iridovirus (RSIV) or infectious spleen and kidney necrosis virus (ISKNV), which is a virus causing infectious aquatic organism disease, in which the genetic marker is represented by SEQ ID NO: 12.

In another aspect, the present invention is directed to a genetic marker for discrimination or detection of red sea bream iridovirus (RSIV), which is a virus causing infectious aquatic organism disease, in which the genetic marker is represented by SEQ ID NO: 13.

In another aspect, the present invention is directed to a genetic marker for discrimination or detection of Koi herpesvirus (KHV), which is a virus causing infectious aquatic organism disease, in which the genetic marker is represented by a nucleotide sequence of SEQ ID NO: 14 or SEQ ID NO: 15.

In still another aspect, the present invention is directed to a primer for discrimination or detection of viral hemorrhagic septicemia virus (VHSV), which is a virus causing infectious aquatic organism disease, in which the primer is represented by a nucleotide sequence of SEQ ID NO: 6.

In yet another aspect, the present invention is directed to a primer for discrimination or detection of red sea bream iridovirus (RSIV) or infectious spleen and kidney necrosis virus (ISKNV), which is a virus causing infectious aquatic organism disease, in which the primer is represented by a nucleotide sequence of SEQ ID NO: 7.

In a further aspect, the present invention is directed to a primer for discrimination or detection of red sea bream iridovirus (RSIV), which is a virus causing infectious aquatic organism disease, in which the primer is represented by a nucleotide sequence of SEQ ID NO: 8.

In a still further aspect, the present invention is directed to a primer for discrimination or detection of Koi herpesvirus (KHV), which is a virus causing infectious aquatic organism disease, in which the primer is represented by a nucleotide sequence of SEQ ID NO: 9 or of SEQ ID NO: 10.

In a yet further aspect, the present invention is directed to a PNA probe for discrimination or detection of viral hemorrhagic septicemia virus (VHSV), which is a virus causing infectious aquatic organism disease, in which the PNA probe is represented by a nucleotide sequence of SEQ ID NO: 1.

In another further aspect, the present invention is directed to a PNA probe for discrimination or detection of red sea bream iridovirus (RSIV) or infectious spleen and kidney necrosis virus (ISKNV), which is a virus causing infectious aquatic organism disease, in which the primer is represented by a nucleotide sequence of SEQ ID NO: 2.

In another further aspect, the present invention is directed to a PNA probe for discrimination or detection of red sea bream iridovirus (RSIV), which is a virus causing infectious aquatic organism disease, in which the primer is represented by a nucleotide sequence of SEQ ID NO: 3.

In another further aspect, the present invention is directed to a PNA probe for discrimination or detection of Koi herpesvirus (KHV), which is a virus causing infectious aquatic organism disease, in which the PNA probe is represented by a nucleotide sequence of SEQ ID NO: 4 or of SEQ ID NO: 5.

The PNA probe according to the present invention may have a reporter and a fluorescence quencher attached to both ends thereof. The fluorescence quencher can quench the fluorescence of the reporter. The reporter may be one or more selected from the group consisting of FAM (6-carboxyfluorescein), Texas red, HEX (2', 4', 5', 7', -tetrachloro-6-carboxy-4,7-dichlorofluorescein), JOE, Cy3, and Cy5. The quencher may be one or more selected from the group consisting of TAMRA (6-carboxytetramethyl-rhodamine), BHQ1, BHQ2 and Dabcyl, but is not limited thereto and preferably Dabcyl (FAM-labeled) can be used as the quencher.

Peptide nucleic acid (PNA) is a DNA analogue having nucleic acid connected by peptide bonds, but not phosphate bonds, and was first synthesized by Nielsen et al. in 1991. PNA is artificially synthesized by a chemical method, but not found in natural systems.

Peptide nucleic acid is one of substances that recognize genes, like LNA (locked nucleic acid) or MNA (morpholino nucleic acid). It is artificially synthesized and has a backbone consisting of polyamide. PNA is greatly excellent in affinity and selectivity and has a high stability for nucleolytic enzyme, and thus is not decomposed by an existing restriction enzyme. In addition, PNA advantageously has high thermal/chemical properties and stability, and thus its storage is easy and it is not easily broken down.

The PNA forms a duplex by its hybridization to a natural nucleic acid having a nucleotide sequence complementary thereto. When they have the same length, the PNA/DNA duplex is more stable than the DNA/DNA duplex and the PNA/RNA duplex is more stable than the DNA/RNA duplex. Furthermore, since the PNA has a single base mismatch that makes the duplex unstable, the ability of the PNA to detect SNP (single nucleotide polymorphism) is better than that of natural nucleic acid.

Furthermore, PNA-DNA binding affinity is very high than DNA-DNA binding affinity, and thus there is a difference in melting point of about 10 to 15° C. even in the presence of one nucleotide mismatch. Using this difference in binding affinity, changes in SNP (single-nucleotide polymorphism) and In/Del nucleotides can be detected.

Although the PNA nucleotide sequence according to the present invention is not particularly limited, it may be constructed to have a length of 12 to 18-mer so as to contain a specific nucleotide sequence (e.g., nucleotide variation or single nucleotide polymorphism (SNP)) depending on the kind of virus. In the present invention, a PNA probe may be designed to have a desired $T_m$ value by adjusting the length of the PNA probe, and even in the case of PNA probes having the same length, the $T_m$ value may be adjusted by changing the nucleotide sequence. Furthermore, since a PNA probe has a binding affinity higher than a DNA probe, it has a higher $T_m$ value. Thus, the PNA probe can be designed to have a length shorter than a DNA probe, so that it can detect even adjacent nucleotide variation or SNP. In a conventional HRM (High Resolution Melt) method, a difference in $T_m$ value from a target nucleic acid is as low as about 0.5° C., and thus an additional analytic program or a minute change or correction in temperature is required, and for this reason, it is difficult to perform analysis, when two or more nucleotide variations or SNPs appear. However, the PNA probe according to the present invention is not influenced by the PNA probe sequence and SNP, and thus makes it possible to perform analysis in a simple and convenient manner.

As described in the present invention, when the PNA probe comprises 14 nucleotides, it preferably has a sequence having one or more nucleotides corresponding to the nucleotide variation or the SNP site of virus, in the middle of the sequence. Furthermore, the PNA probe may have, in the middle portion of the nucleotide sequence, a structural modification including a sequence corresponding to the nucleotide variation or the SNP site of virus, thereby further increasing the difference in melting temperature ($T_m$) from a target nucleic acid to which it perfectly matches.

In another still further aspect, the present invention is directed to a composition and a kit for discrimination or detection of a virus causing infectious aquatic organism disease, which comprises the above-described primer and the above-described PNA probe.

The kit of the present invention may optionally include reagents required for performing a target nucleic acid amplification reaction (e.g., PCR reaction), such as buffer, DNA polymerase cofactor, and deoxyribonucleotide-5-triphosphate. Alternatively, the kit of the present invention may also include various polynucleotide molecules, a reverse transcriptase, various buffers and reagents, and an antibody that inhibits the activities of a DNA polymerase. In addition, in the kit, the optimal amount of the reagent used in a specific reaction can be easily determined by those skilled in the art who have acquired the disclosure set forth herein. Typically, the kit of the invention may be manufactured as a separate package or compartment containing the above mentioned ingredients.

When the kit is used, a single nucleotide mutation and a mutation caused by nucleotide deletion or insertion in a target nucleic acid can be effectively detected by analysis of a melting curve obtained using the PNA, thereby discriminating viral type.

In still another example of the present invention, for 4 kinds of fish viruses causing infectious aquatic organism diseases, gene nucleotide sequences corresponding to PCR products for detection according to the OIE standards were comparatively analyzed, and based on the results of the analysis, a PNA probe represented by each of nucleotide sequences of SEQ ID NOs: 1 to 5 was hybridized to a single-strand PCR amplification product synthesized using a detection primer represented by each of nucleotide sequences of SEQ ID NOs: 6 to 10, thereby obtaining melting curves. From the melting curves, the melting temperature ($T_m$) was determined, so that a virus causing infectious aquatic organism virus could be discriminated and detected.

Therefore, in another yet further aspect, the present invention is directed to a method for discriminating or detecting a virus causing infectious aquatic organism disease, the method comprising the steps of:

(a) extracting a target nucleic acid from a sample;

(b) amplifying a genetic marker nucleotide sequence for an infectious aquatic organism disease-causing virus, contained in the target nucleic acid, by use of a conventional primer pair;

(c) producing a single-strand genetic marker sequence fragment using the amplified genetic marker nucleotide sequence as a template and the above-described primer;

(d) hybridizing the above-described PNA probe to the produced single-strand genetic marker sequence fragment;

(e) obtaining a temperature-dependent melting curve while increasing the temperature of a PNA probe-hybridized product resulting from step (d); and (f) discriminating the viral type of the infectious aquatic organism disease-causing virus or detecting whether or not fish would be infected with the viral type by analyzing the melting curve obtained in step (e) to determine a melting temperature.

In yet another example, the present invention may provide a method for discriminating or detecting viral hemorrhagic septicemia virus (VHSV), the method comprising the steps of:

(a) extracting a target nucleic acid from a sample;

(b) producing a single-strand genetic marker sequence fragment using a genetic marker nucleotide sequence for viral hemorrhagic septicemia virus (VHSV) as a template and the primer represented by a nucleotide sequence of SEQ ID NO: 6;

(c) hybridizing a PNA probe represented by a nucleotide sequence of SEQ ID NO: 1 to the produced single-strand genetic marker sequence fragment;

(d); obtaining a temperature-dependent melting curve while increasing the temperature of a PNA probe-hybridized product resulting from step (c); and (e) discriminating or detecting viral hemorrhagic septicemia virus (VHSV) by analyzing the melting curve obtained in step (d) to determine a melting temperature. In yet another example, the present invention may provide a method for discriminating or detecting red sea bream iridovirus (RSIV), the method comprising the steps of:

(a) extracting a target nucleic acid from a sample;

(b) producing a single-strand genetic marker sequence fragment using a genetic marker nucleotide sequence for red sea bream iridovirus (RSIV) as a template and the primer represented by a nucleotide sequence of SEQ ID NO: 8;

(c) hybridizing a PNA probe represented by a nucleotide sequence of SEQ ID NO: 3 to the produced single-strand genetic marker sequence fragment;

(d); obtaining a temperature-dependent melting curve while increasing the temperature of a PNA probe-hybridized product resulting from step (c); and (e) discriminating or detecting red sea bream iridovirus (RSIV) by analyzing the melting curve obtained in step (d) to determine a melting temperature.

In yet another example, the present invention may provide a method for discriminating or detecting Koi herpesvirus (HSV) bercoiver TK, the method comprising the steps of:

(a) extracting a target nucleic acid from a sample;

(b) producing a single-strand genetic marker sequence fragment using a genetic marker nucleotide sequence for Koi herpesvirus (HSV) bercoiver TK as a template and the primer represented by a nucleotide sequence of SEQ ID NO: 9;

(c) hybridizing a PNA probe represented by a nucleotide sequence of SEQ ID NO: 4 to the produced single-strand genetic marker sequence fragment;

(d); obtaining a temperature-dependent melting curve while increasing the temperature of a PNA probe-hybridized product resulting from step (c); and (e) discriminating or detecting Koi herpesvirus (HSV) bercoiver TK by analyzing the melting curve obtained in step (d) to determine a melting temperature.

In yet another example, the present invention may provide a method for discriminating or detecting Koi herpesvirus (HSV) gray Sph, the method comprising the steps of:

(a) extracting a target nucleic acid from a sample;

(b) producing a single-strand genetic marker sequence fragment using a genetic marker nucleotide sequence for Koi herpesvirus (HSV) gray Sph as a template and the primer represented by a nucleotide sequence of SEQ ID NO: 10;

(c) hybridizing a PNA probe represented by a nucleotide sequence of SEQ ID NO: 5 to the produced single-strand genetic marker sequence fragment;

(d); obtaining a temperature-dependent melting curve while increasing the temperature of a PNA probe-hybridized product resulting from step (c); and (e) discriminating or detecting Koi herpesvirus (HSV) gray Sph by analyzing the melting curve obtained in step (d) to determine a melting temperature.

In the present invention, the single-strand genetic marker sequence fragment may be produced by adding a single strand generation buffer (SSG buffer).

In the present invention, the single strand generation buffer may comprise DNA polymerase, dNTPs (deoxynucleotides) and a stabilizer, in which the DNA polymerase may be Taq polymerase, but is not limited thereto.

In the present invention, step (b) of amplifying the genetic marker nucleotide sequence by use of the conventional primer pair may further comprise adding a TaqMan probe to obtain an amplification curve.

In the present invention, when two or more target nucleic acids are used and the reporter attached to the PNA probe is changed depending on the kind of target nucleic acid, the viral type of one or more viruses causing infectious aquatic organism disease can be discriminated or detected by detecting two or more target nucleic acids.

In the present invention, the amplification may be performed by a real-time PCR (polymerase chain reaction) method.

As used herein, the term "sample" is meant to include various samples. Preferably, a biosample is analyzed using the method of the present invention. More preferably, the sample may be either a sample that is mixed with the viral species, or a sample from an individual (for example, fish or the like) infected with the virus. Biosamples originated from plants, animals, humans, fungi, bacteria and virus can be analyzed. When a mammal- or human-originated sample is analyzed, it may be derived from specific tissues or organs. Representative examples of tissues include connective, skin, muscle, or nervous tissue. Representative examples of organs include eyes, brain, lung, liver, spleen, bone marrow, thymus, heart, lymph, blood, bone, cartilage, pancreas, kidney, gallbladder, stomach, small intestine, testis, ovary, uterus, rectum, nervous system, and gland and internal blood vessels. A biosample to be analyzed includes any cell, tissue or fluid that is derived from a biological origin, or any other medium that can be well analyzed by the present invention. The biosample also includes a sample obtained from foods produced for consumption of humans and/or animals. In addition, the to-be-analyzed biosample includes a body fluid sample, which includes, but not limited to, blood, serum, plasma, lymph, breast milk, urine, feces, ocular fluid, saliva, semen, brain extracts (e.g., pulverized brain), spinal fluid, appendix, spleen, and tonsil tissue extracts.

As used herein, the term "target nucleic acid", "synthetic DNA" or "artificially synthesized oligo" means a nucleic acid sequence (containing SNP or nucleotide variation) to be detected. The target nucleic acid comprises a specific region of the nucleic acid sequence of a "target gene" encoding a protein having physiological and biochemical functions, and is annealed or hybridized to the primer or the probe under hybridization, annealing or amplification conditions.

As used herein, the term "hybridization" means that complementary single-stranded nucleic acids form a double-stranded nucleic acid. Hybridization can occur when the complementarity between two nucleic acid strands is perfect (perfect match) or when some mismatched residues exist. The degree of complementarity necessary for hybridization may vary depending on hybridization conditions, particularly may be controlled by temperature.

In the present invention, the melting curve analysis may be performed by a fluorescence melting curve analysis (FMCA) method.

The PNA probe comprising the reporter and the quencher according to the present invention generates a fluorescent signal after its hybridization to the target nucleic acid. As the temperature increases, the PNA probe is rapidly melted with the target nucleic acid at its suitable melting temperature, and thus the fluorescent signal is quenched. Through analysis of a high-resolution melting curve obtained from the fluorescent signal as a function of this temperature, the presence or absence of a nucleotide modification (including nucleotide variation or SNP) may be detected. If the PNA probe perfectly matches with the nucleotide sequence of the target nucleic acid, it then shows an expected melting temperature ($T_m$) value, but if the PNA probe mismatches with a target nucleic acid in which a nucleotide mutation is present, it shows a melting temperature ($T_m$) value lower than an expected value.

As used herein, the term "nucleotide variation" refers to a change in a nucleotide sequence of a target nucleic acid (e.g., a substitution, deletion or insertion of one or more nucleotides, as well as a single nucleotide polymorphism (SNP)) relative to a reference sequence. The PNA probe of the present invention can analyze a change in a nucleotide sequence of a target nucleic acid, including SNP of the target nucleic acid or a substitution, deletion or insertion of nucleotides of the target nucleic acid through the melting curve analysis.

The PNA probe according to the present invention may have a reporter and a fluorescence quencher attached to both ends. The fluorescence quencher can quench the fluorescence of the reporter. The reporter may be one or more selected from the group consisting of FAM (6-carboxyfluorescein), Texas red, HEX (2', 4', 5', 7', -tetrachloro-6-carboxy-4,7-dichlorofluorescein), JOE, Cy3, and Cy5. The quencher may be one or more selected from the group consisting of TAMRA (6-carboxytetramethyl-rhodamine), BHQ1, BHQ2 and Dabcyl, but is not limited thereto and preferably Dabcyl (FAM-labeled) can be used as the quencher.

The $T_m$ value also changes depending on the difference between the nucleotide sequence of the PNA probe and the nucleotide sequence of a DNA complementary thereto, and thus the development of applications based on this change is easily achieved. The PNA probe is analyzed using a hybridization method different from a method for hybridization of a TaqMan probe, and probes having functions similar to that of the PNA probe include molecular beacon probes and scorpion probes.

A specific nucleotide sequence (e.g., nucleotide variation or SNP) analysis using the PNA probe can be sufficiently achieved using a forward/reverse primer set (according to Office of International Epizootics (OIE) standards for the conventional primer pair) for PCR, a probe comprising nucleotide(s) that recognize(s) the specific nucleotide sequence, and a primer of producing a single-strand genetic marker sequence fragment using a genetic marker nucleotide sequence amplified by the primer set as a template. The PCR may be performed using a conventional method, and after completion of the PCR, a melting process is required. Whenever the melting temperature increases by 0.5° C., the intensity of fluorescence is measured to obtain the $T_m$ value. In particular, general real-time PCR systems are widely known and have an advantage in that purchase of an additional program such as a HRM (high-resolution melting) program or a minute temperature change is not required.

Melting curve analysis according to the present invention is a method of analyzing a double-chain nucleic acid formed of the target nucleic acid DNA or RNA and the probe. This method is called "melting curve analysis", because it is performed by, for example, $T_m$ analysis or the analysis of the melting curve of the double-strand nucleic acid. Using a probe complementary to a specific nucleotide sequence (including nucleotide variation or SNP) of a target to be detected, a hybrid (double-chain DNA) of a target single-chain DNA and the probe is formed. Subsequently, the formed hybrid is heated, and the dissociation (melting) of the hybrid, which results from an increase in the temperature, is detected based on a change in a signal such as absorbance. Based on the results of the detection, the $T_m$ value is determined, thereby determining the presence or absence of the specific nucleotide sequence. The $T_m$ value increases as the homology of the formed hybrid increases, and the $T_m$ value decreases as the homology decreases. For this reason, the $T_m$ value of a hybrid formed of a specific nucleotide sequence of a target to be detected and a probe complementary thereto is previously determined (a reference value for evaluation), and the $T_m$ value of a hybrid formed of the target single-chain DNA of a sample to be detected and the probe is measured (a measured value). If the measured value is approximately equal to the reference value, it can be determined that the probe matches, that is, a specific nucleotide sequence is present in the target DNA. If the measured value is lower than the reference value, the probe mismatches, that is, no mutation is present in the target DNA.

The fluorescent melting curve analysis of the present invention is a method that analyzes a melting curve using a fluorescent material, and more specifically, may analyze the melting curve by using a probe containing a fluorescent material. The fluorescent material may be either a reporter or a quencher, and may preferably be an intercalating fluorescent material.

In the real-time polymerase chain reaction (PCR) method according to the present invention, a fluorescent substance is intercalated into a double-stranded DNA duplex during PCR, and the temperature is increased together with amplification to melt the DNA double strands to thereby reduce the amount of fluorescent substance present between the DNA double strands. The resulting melting curve pattern, particularly the temperature ($T_m$) at which the DNA is melted (denatured), may be analyzed, thereby detecting and/or discriminating the type of virus based on the presence or absence of the specific nucleotide sequence (including nucleotide variation or SNP).

Figure 2:
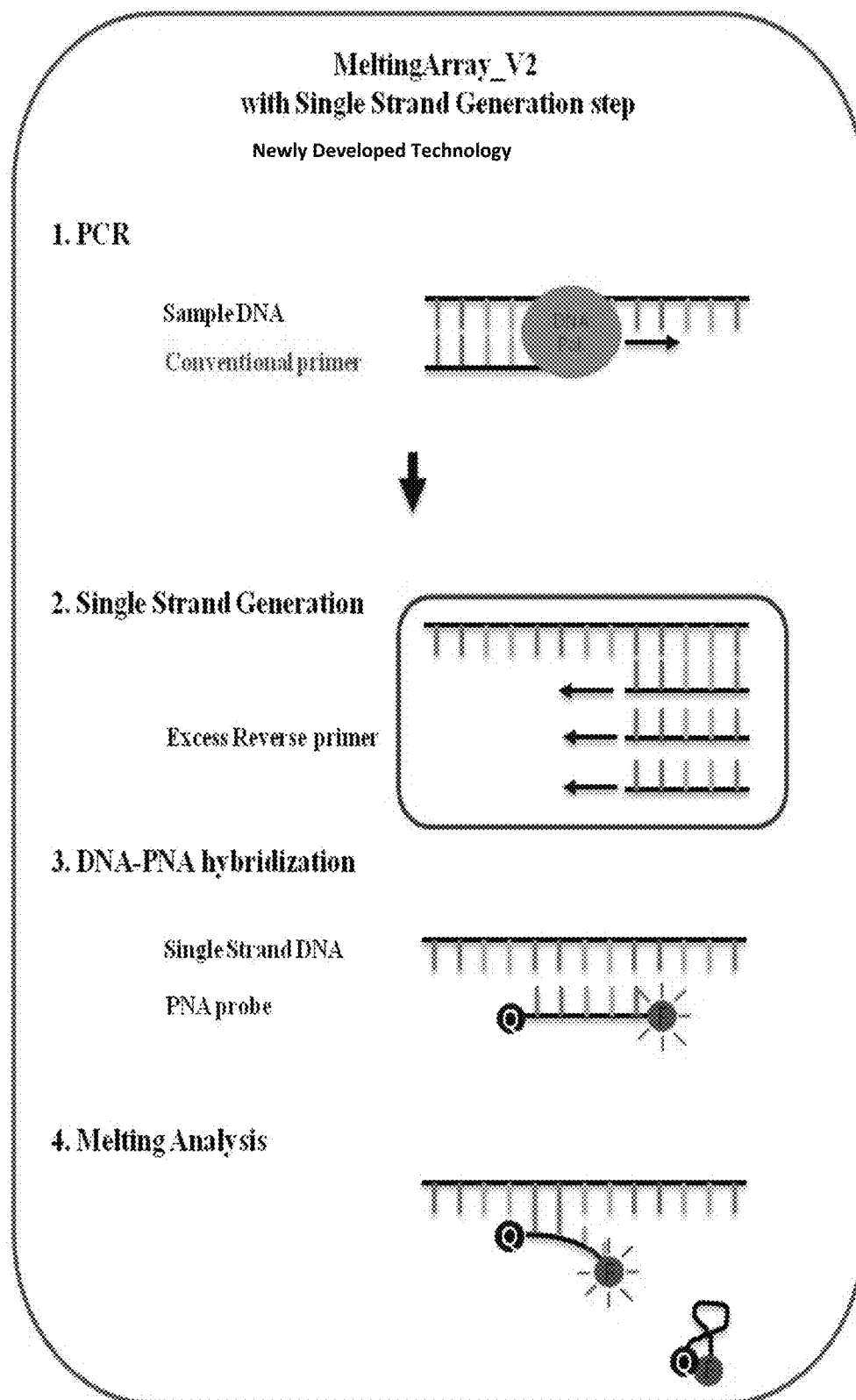
FIG. 2 is a schematic view showing a step of obtaining a melting curve by hybridization of a peptide nucleic acid probe in a method for identifying the type of virus and a method for detecting whether or not an individual would be infected with virus.

FIG. 1 or 2 is a conceptual view illustrating the technical characteristics of MeltingArray for PCR verification according to one embodiment of the present invention. As shown therein, a PNA probe may hybridize to a target nucleic acid, and then generate a fluorescence signal. As the temperature increases, the PNA probe is rapidly melted out from the target nucleic acid at its suitable melting temperature ($T_m$), and thus the fluorescent signal is quenched. According to the present invention, through high-resolution fluorescence melting curve analysis (FMCA) obtained from the fluorescent signal as a results of this temperature change, the presence or absence of a target nucleic acid and a difference in the nucleotide sequence may be detected. If the PNA probe according to the present invention perfectly matches with the nucleotide sequence of the target nucleic acid, it then shows an expected melting temperature ($T_m$) value, but if the PNA probe mismatches with a target nucleic acid in which a nucleotide mutation is present, it then shows a melting temperature ($T_m$) value lower than an expected value. If there is no target nucleic acid, the PNA probe then shows no melting temperature ($T_m$) value.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1: Construction of Genetic Markers for Discrimination and Detection of Viruses Causing Infectious Aquatic Organism Diseases, and Primers and PNA Probes Specific for the Viruses 1-1: Virus Causing Infectious Aquatic Organism Disease: VHSV The sequence of a gene fragment, targeting the N-gene of VHSV and synthesized by "PCR method for detection according to the OIE standards", was analyzed comparatively with the nucleotide sequence registered in the nucleotide database (DB) of the National Center for Biotechnology Information (NCBI) in order to obtain a gene nucleotide sequence for each type of virus.

As a result, the common nucleotide sequence of VHSV represented by 5'-GACATGGGCTTCA-3' (SEQ ID NO: 11) was obtained, and the nucleotide sequence was selected as a genetic marker for discrimination or detection of VHSV.

Furthermore, as a primer for production of a single-strand DNA for the genetic marker, primer 1 represented by SEQ ID NO: 6 was constructed, and as a probe for hybridization to the genetic marker, PNA 1 represented by SEQ ID NO: 1 was constructed.

FIG. 3 is a nucleotide sequence view illustrating the nucleotide sequence of a portion of the gene of VHSV for discrimination/detection and an example of the nucleotide sequence of PNA obtained therefrom. In FIG. 3, the nucleotide sequence corresponding to the PNA probe is indicated by blue color.

1-2: Virus Causing Infectious Aquatic Organism Disease: RSIV/ISKNV

The sequence of a gene fragment of RSIV/ISKNV, synthesized by "PCR protocol 1 (OIE 1) method" for detection according to the OIE standards", was analyzed comparatively with the nucleotide sequence registered in the nucleotide database (DB) of the National Center for Biotechnology Information (NCBI) in order to obtain a gene nucleotide sequence for each type of virus.

As a result, the common nucleotide sequence of RSIV/ISKNV represented by 5'-CCATGTACAACATGCTC-3' (SEQ ID NO: 12) was obtained, and the nucleotide sequence was selected as a genetic marker for discrimination or detection of RSIV/ISKNV.

Furthermore, as a primer for production of a single-strand DNA for the genetic marker, primer 2 represented by SEQ ID NO: 7 was constructed, and as a probe for hybridization to the genetic marker, PNA 2 represented by SEQ ID NO: 2 was constructed.

FIG. 4 is a nucleotide sequence view illustrating the nucleotide sequence of a portion of the gene of RSIV/ISKNV for discrimination/detection and an example of the nucleotide sequence of PNA obtained therefrom. In FIG. 4, the nucleotide sequence corresponding to the PNA probe is indicated by blue color.

1-3: Virus Causing Infectious Aquatic Organism Disease: RSIV

The sequence of a gene fragment of RSIV, synthesized by "PCR protocol 2 (OIE 4) method" for detection according to the OIE standards", was analyzed comparatively with the nucleotide sequence registered in the nucleotide database (DB) of the National Center for Biotechnology Information (NCBI) in order to obtain a gene nucleotide sequence for each type of virus.

As a result, the common nucleotide sequence of RSIV/ISKNV represented by 5'-CCAAGTTCATCATC-3' (SEQ ID NO: 13) was obtained, and the nucleotide sequence was selected as a genetic marker for discrimination or detection of RSIV.

Furthermore, as a primer for production of a single-strand DNA for the genetic marker, primer 3 represented by SEQ ID NO: 8 was constructed, and as a probe for hybridization to the genetic marker, PNA 3 represented by SEQ ID NO: 3 was constructed.

FIG. 5 is a nucleotide sequence view illustrating the nucleotide sequence of a portion of the gene of RSIV for discrimination/detection and an example of the nucleotide sequence of PNA obtained therefrom. In FIG. 5, the nucleotide sequence corresponding to the PNA probe is indicated by blue color.

1-4: Virus Causing Infectious Aquatic Organism Disease: KHV

The sequence of a gene fragment of KHV, synthesized by "Bercoiver TK PCR method" for detection according to the OIE standards", was analyzed comparatively with the nucleotide sequence registered in the nucleotide database (DB) of the National Center for Biotechnology Information (NCBI) in order to obtain a gene nucleotide sequence for each type of virus.

As a result, the common nucleotide sequence of KHV represented by 5'-GTTCTTCCCCGAC-3' (SEQ ID NO: 14) was obtained, and the nucleotide sequence was selected as a genetic marker for discrimination or detection of KHV.

Furthermore, as a primer for production of a single-strand DNA for the genetic marker, primer 4 represented by SEQ ID NO: 9 was constructed, and as a probe for hybridization to the genetic marker, PNA 4 represented by SEQ ID NO: 4 was constructed.

FIG. 6 is a nucleotide sequence view illustrating the nucleotide sequence of a portion of the gene of KHV for discrimination/detection and an example of the nucleotide sequence of PNA obtained therefrom. In FIG. 6, the nucleotide sequence corresponding to the PNA probe is indicated by blue color.

1-5: Virus Causing Infectious Aquatic Organism Disease: KHV

The sequence of a gene fragment of KHV, synthesized by "Gray Sph PCR method" for detection according to the OIE standards", was analyzed comparatively with the nucleotide sequence registered in the nucleotide database (DB) of the National Center for Biotechnology Information (NCBI) in order to obtain a gene nucleotide sequence for each type of virus.

As a result, the common nucleotide sequence of KHV represented by 5'-TCTCAGCAACACC-3' (SEQ ID NO: 15) was obtained, and the nucleotide sequence was selected as a genetic marker for discrimination or detection of KHV.

Furthermore, as a primer for production of a single-strand DNA for the genetic marker, primer 5 represented by SEQ ID NO: 10 was constructed, and as a probe for hybridization to the genetic marker, PNA 5 represented by SEQ ID NO: 5 was constructed.

FIG. 7 is a nucleotide sequence view illustrating the nucleotide sequence of a portion of the gene of KHV for discrimination/detection and an example of the nucleotide sequence of PNA obtained therefrom. In FIG. 7, the nucleotide sequence corresponding to the PNA probe is indicated by blue color.

As a result, the nucleotide sequences of the viral genetic marker, PNA probe and primer according to the present were determined as shown in Table 1 below.

TABLE 1

|  | Name | SEQ ID NO: | Sequences (5'->3') | Modification | Target |
|---|---|---|---|---|---|
| PNA probe | PNA 1 | SEQ ID NO: 1 | TGAAGCCCATGTC | TexasRed, Dabsyl | VHSV |
|  | PNA 2 | SEQ ID NO: 2 | CCATGTACAACATGCTC |  | RSIV, ISKNV |
|  | PNA 3 | SEQ ID NO: 3 | GATGATGAACTTGG |  | RSIV |
|  | PNA 4 | SEQ ID NO: 4 | GTTCTTCCCCGAC |  | KHV Bercoiver TK |
|  | PNA 5 | SEQ ID NO: 5 | TCTCAGCAACACC |  | KHV Gray Sph |
| Primers | primer 1 | SEQ ID NO: 6 | ATGGAAGGAGGAATTCGTGAAGCG | — | VHSV |
|  | primer 2 | SEQ ID NO: 7 | GCACCAACACATCTCCTATC | — | RSIV, ISKNV |
|  | primer 3 | SEQ ID NO: 8 | CGGGGGCAATGACGACTACA | — | RSIV |
|  | primer 4 | SEQ ID NO: 9 | CACCCAGTAGATTATGC | — | KHV Bercoiver TK |
|  | primer 5 | SEQ ID NO: 10 | GACACATGTTACAATGGTCGC | — | KHV Gray Sph |
| Viral marker | VM 1 | SEQ ID NO: 11 | GACATGGGCTTCA | — | VHSV |
|  | VM 2 | SEQ ID NO: 12 | CCATGTACAACATGCTC | — | RSIV, ISKNV |
|  | VM 3 | SEQ ID NO: 13 | CCAAGTTCATCATC | — | RSIV |
|  | VM 4 | SEQ ID NO: 14 | GTTCTTCCCCGAC | — | KHV |
|  | VM 5 | SEQ ID NO: 15 | TCTCAGCAACACC | — | KHV |

TaqMan and PNA probes were labeled with FAM, HEX, TexasRed and Cy5, respectively, such that they would not contain the same fluorescence. Then, PNA probes were constructed using the nucleotide sequence as shown in Table 1 above, a reporter and a quencher. The PNA probes used in the present invention were designed using a PNA probe designer (Applied Biosystems, USA), and the PNA probes were synthesized using a HPLC purification method by Panagene (Korea). The purities of all the synthesized probes were analyzed by mass spectrometry (the unnecessary secondary structures of the probes were avoided for effective binding to target nucleic acids).

Example 2: Optimization of Melting Array Kit for Discrimination or Detection of Virus Causing Infectious Aquatic Organism Disease Using PNA probes and primers constructed in Example 1, amplification curves and melting curves for DNA samples of four kinds of viruses causing infectious aquatic organism diseases were obtained and analyzed to verify PCR products, thereby optimizing the discrimination or detection of the disease-causing viruses. Herein, a TaqMan probe (and a conventional primer pair corresponding thereto) for discrimination or detection of the disease-causing viruses according to the OIE (Office of International Epizootics) standards may be used.

A MeltingArray reaction was performed using a CFX96™ real-time system (BIO-RAD, USA). To produce a single-strand target nucleic acid from the PCR product, a single-strand generation buffer (SSG buffer) and a single primer complementary to the binding strand of the probe were used. The composition of the SSG buffer comprised 2× nTaq-HOT (0.2 units/μl), nTaq-HOT buffer (containing 4 mM MgCl$_2$), a dNTP mixture (A, T, G and C; 0.4 mM for each) and a stabilizer.

The composition of reactants for the MeltingArray reaction is shown in Table 2 below. A master mix for a MeltingArray kit was prepared, and then 1 to 3 μL of the PCR product was added thereto, followed by analysis.

TABLE 2

| Composition | Content |
| --- | --- |
| 2X SSG buffer | 10 μL |
| Oligomer mix (PNA probe, primer) | 1.5 μL |
| Template(Template, PCR product) | 1~3 μL |
| Distilled water | up to 20 μL |

Table 3 shows conditions for hybridization reaction of reactants. Specifically, Table 3 shows a step of producing a single-strand DNA from the PCR product, a denaturation step, and a process of hybridizing the PNA probe and increasing the temperature of the hybridized product.

TABLE 3

| Steps | Temperature(° C.) | Reaction time and cycle | |
| --- | --- | --- | --- |
| Single strand generation) | 95 | 5-10 min | |
| | 95 | 30 sec | 15-20 cycle |
| | 56 | 30 sec | |
| | 76 | 30 sec | |
| Denaturation | 95 | 1 min | |
| Probe binding | 75 | 30 sec | |
| | 55 | 30 sec | |
| Melting | 45 to 80 | Increment 1.0° C., 5 sec (TexasRed) | |

As a result, as can be seen in FIG. 8, viruses causing infectious aquatic organism diseases could be discriminated or detected by analysis of melting curves obtained using five kinds of PNA probes.

Example 3: Method for Discriminating or Detecting Virus Based on Melting Peak Obtained Using PNA Probe When the viral type for a unknown viral DNA sample is to be discriminated or detected using the PNA probes according to the present invention, a table listing scores at different melting temperatures as shown in Table 4 below can be previously prepared and can be used.

After melting curve analysis was performed as described in Example 2, the obtained fluorescence signal and $T_m$ value were digitized according to the temperature at which a perfect match appeared. Specifically, the range of perfect match temperature ±2° C. is made, and when the $T_m$ value for a unknown viral DNA sample is within this range, the type of virus in the viral sample can be identified and discriminated.

TABLE 4

| Fluorescent material of PNA probe | Tm(° C.) | Kind of detectable virus |
| --- | --- | --- |
| TexasRed | 65 | VHSV |
| | 65 | RSIV, ISKNV |
| | 66 | RSIV |
| | 60 | KHV |
| | 62 | KHV |

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A PNA probe consisting of SEQ ID NO: 3, for discrimination or detection of red sea bream iridovirus (RSIV) which is a virus causing infectious aquatic organism disease.

2. A PNA probe consisting of SEQ ID NO: 3 with one or more of a reporter and a quencher attached thereto, wherein the probe is for discrimination or detection of red sea bream iridovirus (RSIV) which is a virus causing infectious aquatic organism disease.

3. A composition for discrimination or detection of red sea bream iridovirus (RSIV), the composition comprising: a primer consisting of SEQ ID NO: 8 and a PNA probe consisting of SEQ ID NO: 3.

4. A kit for discrimination or detection of Red sea bream iridovirus (RSIV), the kit comprising: a primer consisting of SEQ ID NO: 8; and a PNA probe consisting of SEQ ID NO: 3.

5. A method for detecting Red sea bream iridovirus (RSIV), the method comprising the steps of:
 (a) extracting a target nucleic acid from a fish sample;
 (b) amplifying a genetic marker nucleotide sequence for Red sea bream iridovirus (RSIV) contained in the target nucleic acid by use of a primer pair capable of amplifying a fragment consisting of SEQ ID NO: 19;
 (c) producing a single-strand genetic marker sequence fragment using the amplified genetic marker nucleotide sequence as a template and a primer consisting of SEQ ID NO: 8;
 (d) hybridizing a PNA probe consisting of a reporter and quencher labeled SEQ ID NO: 3 to the produced single-strand genetic marker sequence fragment;
 (e) obtaining a temperature-dependent melting curve while increasing the temperature of a PNA probe-hybridized product resulting from step (d); and
 (f) detecting whether or not the fish sample is infected with red sea bream iridovirus (RSIV) by analyzing the melting curve obtained in step (e) to determine a melting temperature.

6. The method of claim 5, the single-strand genetic marker sequence fragment in step (c) is produced by adding a single strand generation buffer (SSG buffer).

7. The method of claim 6, wherein the single strand generation buffer comprises DNA polymerase, dNTPs (deoxynucleotides) and a stabilizer.

8. The method of claim 5, wherein step (b) of amplifying the genetic marker nucleotide sequence by use of the primer pair further comprises adding a TaqMan probe to obtain an amplification curve.

* * * * *